United States Patent [19]

Arzbaecher

[11] Patent Number: 5,607,418
[45] Date of Patent: Mar. 4, 1997

[54] IMPLANTABLE DRUG DELIVERY APPARATUS

[75] Inventor: Robert C. Arzbaecher, Chicago, Ill.

[73] Assignee: Illinois Institute of Technology, Chicago, Ill.

[21] Appl. No.: 518,032

[22] Filed: Aug. 22, 1995

[51] Int. Cl.⁶ .................................................. A61K 9/22
[52] U.S. Cl. ...................... 604/891.1; 604/132; 604/134; 604/141; 128/DIG. 12
[58] Field of Search ................................... 604/131, 132, 604/134, 141, 890.1, 891.1; 128/DIG. 12

[56] References Cited

U.S. PATENT DOCUMENTS

| | | | |
|---|---|---|---|
| 4,221,219 | 9/1980 | Tucker | 604/141 |
| 4,265,241 | 5/1981 | Portner et al. | 604/134 |
| 4,360,019 | 11/1982 | Portner et al. | 604/891.1 |
| 4,505,710 | 3/1985 | Collins | 604/131 |
| 4,525,165 | 6/1985 | Fischell . | |
| 4,544,371 | 10/1985 | Dormandy, Jr. et al. . | |
| 4,718,893 | 1/1988 | Dorman et al. | 604/134 |
| 4,772,263 | 9/1988 | Dorman et al. | 604/134 |
| 4,931,050 | 6/1990 | Idriss . | |
| 5,049,141 | 9/1991 | Olive . | |
| 5,053,031 | 10/1991 | Borsanyi . | |
| 5,067,943 | 11/1991 | Burke . | |
| 5,085,644 | 2/1992 | Watson et al. . | |
| 5,207,666 | 5/1993 | Idriss et al. . | |
| 5,328,460 | 7/1994 | Lord et al. | 128/DIG. 12 |
| 5,368,571 | 11/1994 | Horres | 604/131 |
| 5,382,236 | 1/1995 | Otto et al. . | |

FOREIGN PATENT DOCUMENTS 0278496  5/1990  Germany ............................... 604/131

Primary Examiner—David Isabella
Assistant Examiner—Mark O. Polutta
Attorney, Agent, or Firm—Speckman, Pauley & Fejer

[57] ABSTRACT

An implantable drug delivery apparatus including a housing that has a housing chamber. An outer deformable body having a reserve chamber is mounted within the housing chamber. An inner deformable body having a dispensing chamber is mounted within the reserve chamber. A dispensing valve is actuated to an open position to allow a fluidic drug to flow from the dispensing chamber, through the dispensing valve and through a catheter into a body of a patient. The fluidic drug is discharged from the dispensing chamber at a dispensing mass flowrate which is greater than a refilling mass flowrate of the fluidic drug passing from the reserve chamber to the dispensing chamber, when the dispensing valve is in an open position. When the dispensing valve is in a closed position, the fluidic drug is prevented from discharging from the dispensing chamber while a recharging amount of the fluidic drug is capable of flowing from the reserve chamber to the dispensing chamber, until the dispensing chamber is at least partially filled. The outer deformable body is normally forced or urged in a direction or manner that tends to reduce a volume of the reserve chamber.

25 Claims, 1 Drawing Sheet

IMPLANTABLE DRUG DELIVERY APPARATUS

This invention was made with U.S. Government support under Grant Number 5-RO1-HL32131 awarded by the National Institutes of Health. The U.S. Government has certain rights in this invention.

BACKGROUND OF THE INVENTION

Field of the Invention

This invention relates to an implantable drug delivery apparatus that can be actuated and refilled without removing a housing structure from a patient. The implantable drug delivery apparatus of this invention has relatively few moving mechanical components and thus is relatively inexpensive, reliable and safe.

Description of Prior Art

Existing implantable drug pumps operate with a single bellows and a relatively complex valve arrangement. Use of a single valve in such conventional implantable drug pumps is relatively unsafe because if the valve sticks in an open position, the patient receives an overdose of drug. Conventional implantable drug pump systems thus require multiple valves, motorized peristaltic mechanisms, roller mechanisms and/or other relatively complex mechanical mechanisms to assure positive closure of the discharge catheter after delivery of an intended dose of drug.

U.S. Pat. No. 5,382,236 discloses an implantable infusion pump with a flexible bellows medication container which is mounted within a sealed enclosure. A propellant gas acts upon the bellows medication container to force drug through a capillary tube.

Many conventional implantable drug pumps employ a bellows element mounted within a housing and a two-phase fluid or propellant occupies a void between the bellows and a housing. For example, U.S. Pat. No. 5,049,141 teaches an apparatus that uses a two-phase fluid to actuate a titanium diaphragm. U.S. Pat. No. 5,207,666 teaches a fluid metering device for an implantable drug delivery system which uses a bellows-type reservoir to deliver a drug to the metering device.

Two-phase or liquid/vapor fluids are used in conventional implantable infusion pumps for the purpose of maintaining a constant pressure on the drug so that the drug flows through a capillary at a relatively constant flowrate.

SUMMARY OF THE INVENTION

It is one object of this invention to provide an implantable drug delivery apparatus which has relatively few moving mechanical components and which is relatively inexpensive, durable and long-lasting.

It is another object of this invention to provide a safe implantable drug delivery apparatus which in a failed condition is limited to a delivery mass flowrate of a fluidic drug which is well below a clinically approved level, for example when a dispensing valve fails in an open position.

It is another object of this invention to provide an implantable drug delivery apparatus which automatically refills a dispensing chamber following discharge of a dispensing portion of the fluidic drug.

It is still another object of the invention to provide an implantable drug delivery apparatus which has two deformable bodies, one positioned within the other, wherein the one is activated from forces transmitted by the other.

In one preferred embodiment according to this invention, the implantable drug delivery apparatus has an outer bellows which defines a reserve chamber and has an inner bellows which defines a dispensing chamber. The dispensing chamber is sized to accommodate a prescribed amount or dosage of fluidic drug. The inner bellows is preferably mounted within the reserve chamber of the outer bellows. A discharge of the inner bellows is preferably in communication with an inlet of a dispensing valve. When the dispensing valve is open, the fluidic drug flows from the dispensing chamber, through the dispensing valve, into a catheter and then into a body of a patient.

The dispensing chamber is preferably filled with a predetermined amount or dosage of the fluidic drug. When the dispensing valve is open, the inner bellows discharges the fluidic drug from the dispensing chamber through the dispensing valve, due to the resultant forces from the outer bellows that act through the medium of the fluidic drug upon the inner bellows. When the dispensing valve is closed, a return bias force within the inner bellows returns the inner bellows to an expanded position which replenishes the dispensing chamber with a recharged amount or dosage of the fluidic drug received from the reserve chamber.

In one preferred embodiment according to this invention, a propellant at least partially fills a housing chamber defined between the outer bellows and a housing in which the outer bellows is mounted. For example, a fluorocarbon in the saturated vapor/liquid state at least partially fills the housing chamber and thus exerts a force upon the outer bellows in a direction or manner that tends to reduce the volume of the reserve chamber.

In one preferred embodiment according to this invention, one flow restrictor is positioned so that an inlet is in communication with the reserve chamber and an outlet is in communication with the dispensing chamber, and another flow restrictor is positioned so that an inlet is in communication with the dispensing chamber and an outlet is in communication with an inlet of the dispensing valve. The flow restrictors are preferably designed and sized so that the fluidic drug is discharged from the dispensing chamber at a mass dispensing flowrate which exceeds a refilling mass flowrate of the fluidic drug which passes from the reserve chamber to the dispensing chamber, when the dispensing valve is an open position. When the dispensing valve is in a closed position, the flow restrictor between the reserve chamber and the dispensing chamber is preferably designed and sized so that fluidic drug flows from the reserve chamber to the dispensing chamber, until the dispensing chamber is at least partially filled.

The housing preferably has a filling septum which is mounted with respect to the housing. A surface of the septum is preferably exposed to the reserve chamber. A hypodermic needle and syringe can be used to pierce the filling septum and recharge the reserve chamber with the fluidic drug, without removing the housing from the body of the patient. The fluidic drug within the dispensing chamber can be delivered through the catheter into the body of the patient by actuating the dispensing valve, preferably with an actuator that is either external or internal with respect to the body of the patient. For example, a transcutaneous magnetic actuator or an implanted electronic actuator can be used to open and close the dispensing valve.

The flow restrictor can be designed and constructed as any suitable flow restriction device known to those skilled in the art. For example, each flow restrictor may comprise an extended length of conduit which offers a suitable lengthto-diameter ratio and thus sufficient pressure drop, a nozzle, an orifice plate, a one-way valve, or any other similar flow restriction device.

The implantable drug delivery apparatus according to this invention offers a much safer delivery apparatus than any conventional implantable drug delivery apparatus which uses relatively complex valve mechanisms and control schemes. The flow restrictors of this invention are preferably sized so that the flow of fluidic drug discharged from the dispensing chamber is from about 10 times to about 150 times greater than the flow of fluidic drug from the reserve chamber to the dispensing chamber. The implantable drug delivery apparatus according to this invention can be used for ambulatory intravenous drug infusion in the treatment of recurrent episodes of diseases such as paroxysmal atrial fibrillation, orthostatic hypotension, epilepsy and the like.

BRIEF DESCRIPTION OF THE DRAWINGS

The above-mentioned and other features and objects of this invention will be better understood from the following detailed description taken in conjunction with the drawings wherein.

DESCRIPTION OF PREFERRED EMBODIMENTS

Figure 1:
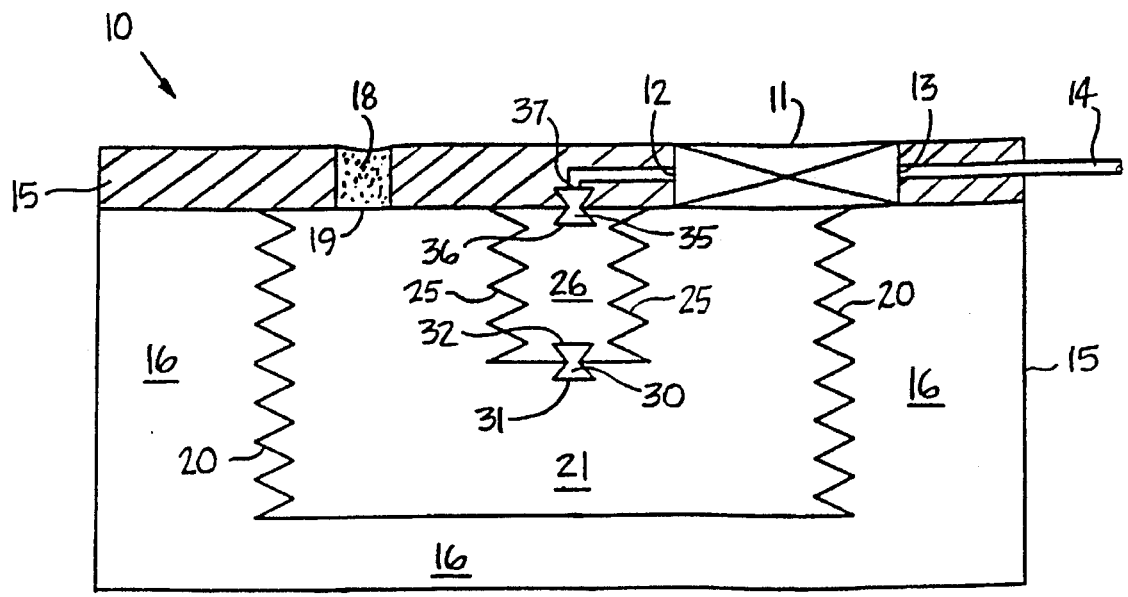
FIG. 1 is a schematic diagram showing one preferred embodiment of an apparatus according to this invention.

Referring to one preferred embodiment of this invention as schematically shown in FIG. 1, implantable drug delivery apparatus 10 comprises housing 15 which defines housing chamber 16. Housing 15 is preferably sealed, such as hermetically sealed, in a manner which is suitable for implanting within a human body. Sealed housings and their construction are known by those skilled in the art of designing and constructing implantable devices. It is apparent that housing 10 can have any suitable shape which accommodates its intended purpose.

Outer deformable body 20 defines reserve chamber 21. Inner deformable body 25 defines dispensing chamber 26. According to one preferred embodiment of this invention, inner deformable body 25 is mounted within reserve chamber 21, as shown in FIGS. 1 and 2.

Figure 2:
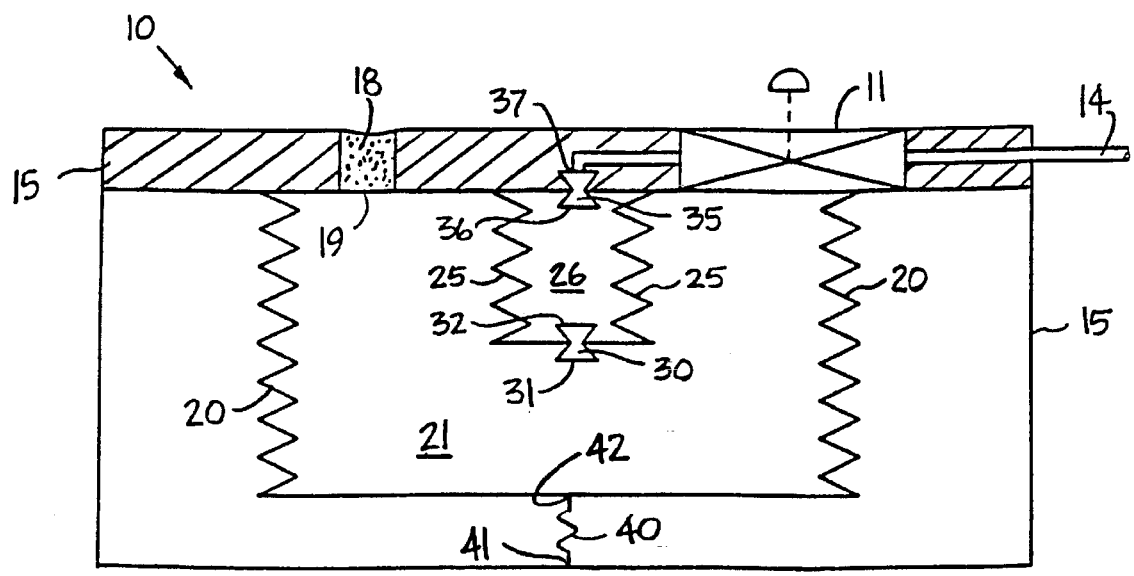
FIG. 2 is a schematic diagram showing another preferred embodiment of an apparatus according to this invention.

According to preferred embodiments of this invention as shown in FIGS. 1 and 2, outer deformable body 20 and inner deformable body 25 comprise a bellows. A bellows is one type of deformable body that is particularly suitable for implantable drug delivery apparatus 10 according to this invention. The bellows can be constructed of any suitable metal, such as titanium or stainless steel, any suitable elastomeric material, such as rubber or silicone, or any other suitable material that allows the deformable body to have a return bias force. The material used to construct the bellows of this invention should be appropriate for implantation within a human body.

In other preferred embodiments according to this invention, outer deformable body 20 and/or inner deformable body 25 can comprise any other suitable hollow body which can be deformed and which has a return bias force that allows the deformable body to approximately return to its initial condition after a deforming force is removed. For example, outer deformable body 20 and/or inner deformable body 25 may comprise any elastomeric bladder or any other similar device. It should be noted, as discussed below, that outer deformable body 20 need not have a return bias force.

As shown in FIG. 1, discharge 13 of dispensing valve 11 is in communication with catheter 14. When dispensing valve 11 is in an open position, dispensing chamber 26 is in communication with inlet 12 of dispensing valve 11, and thus in communication with catheter 14. When dispensing valve 11 is in an open position, a fluidic drug flows from dispensing chamber 26, through flow restrictor 35, dispensing valve 11 and catheter 14, and then is discharged into a body of a patient. As shown in FIG. 2, dispensing valve 11 can be actuated from an external position with respect to the body of a patient. For example, dispensing valve 11 can be actuated with an external magnet or with an implanted electronic module that communicates with and controls an actuator connected to dispensing valve 11, as shown in FIG. 2, in any suitable manner known to those skilled in the art of control components for implantable medical devices.

Force means are used to normally urge or force outer deformable body 20 in a direction or manner that tends to reduce a volume of reserve chamber 21. In one preferred embodiment according to this invention, the force means comprise housing chamber 16 being at least partially filled with a propellant or compressible gas, such as a fluorocarbon in the saturated vapor/liquid state. With such saturated vapor/liquid fluorocarbon, the pressure of the saturated vapor/liquid fluorocarbon within housing chamber 16 remains constant at constant temperatures. Because implantable drug delivery apparatus 10 is preferably implanted within a human body, the temperature of fluid within housing chamber 16 remains approximately constant. Thus, the saturated vapor/liquid fluorocarbon provides a constant force urging outer deformable body 20 in a direction or manner that tends to reduce the volume of reserve chamber 21. The saturated vapor/liquid fluorocarbon is particularly suitable because it provides a constant pressure which does not vary, outside of given tolerances, as a function of the volume of housing chamber 16. In preferred embodiments of this invention which use a saturated vapor/liquid fluorocarbon as the force means, outer deformable body 20 can have but does not necessarily require a return bias force.

Although the saturated vapor/liquid fluorocarbon or other similar propellant or compressible fluid stabilizes the pressure within housing chamber 16 and thus acts as a system buffer or compensator, it is apparent that other force means can be used independently or in combination with the saturated vapor/liquid fluorocarbon to normally urge or force outer deformable body 20 in a direction or manner that tends to reduce the volume of reserve chamber 21. For example, as shown in FIG. 2, spring 40 can have end 41 fixed with respect to housing 15 and end 42 fixed with respect to outer deformable body 20, so that spring 40 normally forces or urges outer deformable body 20 in a direction or manner that reduces the volume of reserve chamber 21. It is apparent that spring 40 can be designed to provide a constant force which acts upon outer deformable body 20. The force means may also comprise outer deformable body 20 constructed as a bellows which itself has a return bias force. However, without a pressurized fluorocarbon within housing chamber 16, the resulting fluidic drug flow being discharged from dispensing chamber 26 may not be as constant as with a pressurized fluorocarbon.

According to one preferred embodiment of this invention, flow means are used to discharge the fluidic drug from dispensing chamber 26 at a dispensing mass flowrate which is greater than a refilling mass flowrate of the fluidic drug passing from reserve chamber 21 to dispensing chamber 26, when dispensing valve 11 is in an open position. The flow means preferably also prevent the fluidic drug from discharging from dispensing chamber 26 and allowing the fluidic drug to flow from reserve chamber 21 to dispensing chamber 26, until dispensing chamber 26 is at least partially filled with the fluidic drug, when dispensing valve 11 is in a closed position.

In one preferred embodiment according to this invention, the flow means comprise flow restrictor 35 having inlet 36 in communication with dispensing chamber 26 and outlet 37 in communication with inlet 12 of dispensing valve 11. The flow means may also comprise flow restrictor 30 having inlet 31 in communication with reserve chamber 21 and outlet 32 in communication with dispensing chamber 26.

Flow restrictor 30 and/or flow restrictor 35 can be any suitable flow restriction device that provides a pressure drop as the fluidic drug flows across the flow restriction device. In one preferred embodiment according to this invention, the flow restriction device comprises an extended length of conduit, such as a coiled tube or capillary constructed of stainless steel or another material suitable for implantation. The extended length of conduit preferably has a relatively high length-to-diameter ratio so that a sufficient pressure drop is achieved. It is apparent that the type of material, length of conduit and/or diameter of conduit can be varied to achieve various pressure drops and thus various mass flowrates at given pressures and temperatures.

In another preferred embodiment according to this invention, the flow restriction device comprises a nozzle, such as a converging-diverging nozzle. In another preferred embodiment according to this invention, the flow restriction device comprises an orifice plate positioned between the respective chambers or other voids. In still another preferred embodiment according to this invention, the flow restriction device comprises a one-way valve arranged to allow the fluidic drug to flow from one particular chamber or void to another particular chamber or void.

The flow means, such as the extended length of conduit, the nozzle, the orifice plate or the one-way valve is preferably designed so that a dispensing mass flowrate of the fluidic drug discharged from dispensing chamber 26 is in a range of about 10 times to about 150 times, depending upon the type of fluidic drug, the refilling mass flowrate of fluidic drug flowing from reserve chamber 21 to dispensing chamber 26. As an example, if dispensing chamber 26 has a volume of 4 ml, the dispensing mass flowrate is at 0.4 ml/min, the fluorocarbon pressure is at 400 mm Hg and the refilling mass flowrate at 8 ml/day, it would take approximately ten minutes to discharge the fluidic drug from dispensing chamber 26, and approximately one-half day to refill dispensing chamber 26 from reserve chamber 21. Thus, if dispensing valve 11 fails in an open position, the resulting rate of drug delivery to the patient could be well below a clinically approved rate, based upon the particular drug being delivered.

According to one preferred embodiment of this invention, it is apparent that as dispensing chamber 26 is being discharged it is also being refilled but at a much lesser mass flowrate. Although refilling is occurring while discharge is also occurring, the actual volume of fluidic drug delivered to a patient is slightly greater than the volume of dispensing chamber 26. However, it is apparent that the size of dispensing chamber 26 can be designed to compensate for the volume of fluidic drug that flows into dispensing chamber 26 during the delivery time of the fluidic drug.

According to another preferred embodiment of this invention, implantable drug delivery apparatus 10 comprises fill means for filling reserve chamber 21 with the fluidic drug, while implantable drug delivery apparatus 10 is implanted within a patient. The fill means may comprise filling septum 18 which is mounted with respect to housing 15. Septum surface 19 is preferably exposed to reserve chamber 21, as shown in FIG. 1. Filling septum 18 can accommodate a hypodermic needle and syringe. Any suitable septum which is known by those skilled in the art can be used to recharge reserve chamber 21.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

I claim:

1. An implantable drug delivery apparatus comprising:

a housing having a housing chamber, an outer deformable body having a reserve chamber, said outer deformable body mounted within said housing chamber, an inner deformable body having a dispensing chamber, said inner deformable body mounted within said reserve chamber;

a dispensing valve, a catheter in communication with a valve discharge of said dispensing valve;

flow means for discharging a fluidic drug from said dispensing chamber at a dispensing mass flowrate which exceeds a refilling mass flowrate of said fluidic drug passing from said reserve chamber to said dispensing chamber when said dispensing valve is in an open position, and for preventing said fluidic drug from discharging from said dispensing chamber and allowing said fluidic drug to flow from said reserve chamber to said dispensing chamber until said dispensing chamber is at least partially filled when said dispensing valve is in a closed position; and force means for normally urging said outer deformable body in a manner that tends to reduce a volume of said reserve chamber.

2. An implantable drug delivery apparatus according to claim 1 wherein said housing is hermetically sealed.

3. An implantable drug delivery apparatus according to claim 1 wherein said outer deformable body comprises a bellows.

4. An implantable drug delivery apparatus according to claim 1 wherein said inner deformable body comprises a bellows.

5. An implantable drug delivery apparatus according to claim 1 further comprising fill means for filling said reserve chamber with said fluidic drug with the drug delivery apparatus implanted within a patient.

6. An implantable drug delivery apparatus according to claim 5 wherein said fill means comprises a filling septum mounted with respect to said housing and having a septum surface exposed to said reserve chamber.

7. An implantable drug delivery apparatus according to claim 1 further comprising an actuator mechanically coupled to said dispensing valve for actuating said dispensing valve between said open position and said closed position.

8. An implantable drug delivery apparatus according to claim 1 wherein said flow means comprises a flow restriction device having an inlet in communication with said dispensing chamber and an outlet in communication with a valve inlet of said dispensing valve.

9. An implantable drug delivery apparatus according to claim 8 wherein said flow restriction device comprises an extended length of conduit.

10. An implantable drug delivery apparatus according to claim 8 wherein said flow restriction device comprises a nozzle.

11. An implantable drug delivery apparatus according to claim 8 wherein said flow restriction device comprises an orifice plate.

12. An implantable drug delivery apparatus according to claim 8 wherein said flow restriction device comprises a one-way valve arranged to allow said fluidic drug to flow from said dispensing chamber to said valve inlet of said dispensing valve.

13. An implantable drug delivery apparatus according to claim 1 wherein said flow means comprises a flow restriction device having an inlet in communication with said reserve chamber and an outlet in communication with said dispensing chamber.

14. An implantable drug delivery apparatus according to claim 13 wherein said flow restriction device comprises an extended length of conduit.

15. An implantable drug delivery apparatus according to claim 13 wherein said flow restriction device comprises a nozzle.

16. An implantable drug delivery apparatus according to claim 13 wherein said flow restriction device comprises an orifice plate.

17. An implantable drug delivery apparatus according to claim 13 wherein said flow restriction device comprises a one-way valve arranged to allow said fluidic drug to flow from said reserve chamber to said dispensing chamber.

18. An implantable drug delivery apparatus according to claim 1 wherein said flow means comprises a first flow restriction device having a first inlet in communication with said dispensing chamber and a first outlet in communication with a valve inlet of said dispensing valve, and a second flow restriction device having a second inlet in communication with said reserve chamber and a second outlet in communication with said dispensing chamber.

19. An implantable drug delivery apparatus according to claim 1 wherein said flow means is designed so that said dispensing mass flowrate is in a range of about 10 times to about 150 times said refilling mass flowrate.

20. An implantable drug delivery apparatus according to claim 1 wherein said force means comprises said outer deformable body having a compressive bias force which urges said outer deformable body in a direction that reduces said volume of said reserve chamber.

21. An implantable drug delivery apparatus according to claim 20 wherein said outer deformable body comprises a bellows.

22. An implantable drug delivery apparatus according to claim 1 wherein said force means comprises said housing chamber at least partially filled with a propellant.

23. An implantable drug delivery apparatus according to claim 1 wherein said force means comprises said housing chamber at least partially filled with a compressible fluid.

24. An implantable drug delivery apparatus according to claim 1 wherein said force means comprises a spring having one end attached with respect to said outer deformable body and an opposite end attached with respect to said housing.

25. An implantable drug delivery apparatus according to claim 1 wherein a pressure of said fluidic drug within said dispensing chamber is increased as said outer deformable body is urged in said manner.

\* \* \* \* \*

UNITED STATES PATENT AND TRADEMARK OFFICE
CERTIFICATE OF CORRECTION

| | | |
|---|---|---|
| PATENT NO. | : 5,607,418 | Page 1 of 1 |
| APPLICATION NO. | : 08/518032 | |
| DATED | : March 4, 1997 | |
| INVENTOR(S) | : Robert C. Arzbaecher | |

It is certified that error appears in the above-identified patent and that said Letters Patent is hereby corrected as shown below:

In the Specification

In line 5 of column 1, delete "5-RO1-HL32131" and insert -- R41 DA09631-01 --

Signed and Sealed this
Twelfth Day of August, 2014

Michelle K. Lee
*Deputy Director of the United States Patent and Trademark Office*